United States Patent
Motamedi et al.

(10) Patent No.: US 8,210,682 B2
(45) Date of Patent: Jul. 3, 2012

(54) METHOD AND APPARATUS FOR EARLY DIAGNOSIS OF ALZHEIMER'S USING NON-INVASIVE EYE TOMOGRAPHY BY TERAHERTS

(76) Inventors: Manouchehr Motamedi, Sugarland, TX (US); Ali Dabiri, Brier, WA (US)

(*) Notice: Subject to any disclaimer, the term of this patent is extended or adjusted under 35 U.S.C. 154(b) by 301 days.

(21) Appl. No.: 12/655,592

(22) Filed: Jan. 4, 2010

(65) Prior Publication Data
US 2010/0110381 A1 May 6, 2010

Related U.S. Application Data

(63) Continuation-in-part of application No. 11/880,911, filed on Jul. 26, 2007, now Pat. No. 7,641,343.

(51) Int. Cl.
*A61B 3/00* (2006.01)
*A61B 3/10* (2006.01)
(52) U.S. Cl. ........................ 351/246; 351/221
(58) Field of Classification Search .................. 351/221, 351/246
See application file for complete search history.

(56) References Cited

U.S. PATENT DOCUMENTS

| | | | |
|---|---|---|---|
| 5,430,509 A * | 7/1995 | Kobayashi | 351/221 |
| 5,684,561 A * | 11/1997 | Yancey | 351/209 |
| 6,293,674 B1 * | 9/2001 | Huang et al. | 351/221 |
| 6,381,015 B1 * | 4/2002 | Sonehara et al. | 356/497 |
| 2007/0030115 A1 * | 2/2007 | Itsuji et al. | 340/5.8 |
| 2007/0255141 A1 * | 11/2007 | Esenaliev et al. | 600/475 |
| 2009/0027689 A1 * | 1/2009 | Yun et al. | 356/511 |
| 2009/0279098 A1 * | 11/2009 | Ohbayashi et al. | 356/478 |

* cited by examiner

*Primary Examiner* — Jordan Schwartz

(57) ABSTRACT

The primary objective of the present method and apparatus is to provide a transportable diagnosis system for a reliable method to examine the conditions of a human eye lens. The method provides precise and safe technique for the early diagnosis of Alzheimer's Disease (AD) which is not involved brain surgery or biopsy. The detection of deposited amyloid plaque in the eyes of the patient has been discovered to be a possible diagnosis solution. The disclosed method uses Terahertz waves in both time and frequency domains instead of laser for scanning the eye of the AD patient to precisely image the amyloid layer non-evasively in real time and to map the deposited plaque with high resolution which can easily distinguish the abnormality of an AD patient with the comparison of the patient eye lens test to the available signature of a normal person and the signature of a person with common age-related cataracts.

9 Claims, 4 Drawing Sheets

Focused on RNFL

Lens Characteristics:
D = 9 mm, T = 4 mm
n 1.38-1.4 (Focusing)

D=diameter, T=thichness, n=index of reflection

Focused on RNFL

METHOD AND APPARATUS FOR EARLY DIAGNOSIS OF ALZHEIMER'S USING NON-INVASIVE EYE TOMOGRAPHY BY TERAHERTS

Continuous-in-part of application Ser. No. 11/880,911, filed Jul. 26, 2007, now U.S. Pat. No. 7,641,343.

FIELD OF THE DISCLOSED METHOD AND APPARATUS

This method and apparatus is related to non-invasively detecting early development of Alzheimer by scanning patient eye and, in particular, relates to a method and apparatus for diagnosis and tomography using Terahertz imaging.

BACKGROUND OF PRIOR ARTS

Alzheimer's disease (AD) in a medical term is classified as a form of dementia, a group of conditions that gradually destroy brain cells. Alzheimer's generally appears in older persons, continuing steadily to disorder brain and gradually destroys a person's memory and ability to make judgments, communicate and carry out daily activities. Scientists now believe that the cause of AD is most likely due to the concentration of Beta-amyloid deposited in some part of the brain. As Alzheimer's progresses, patients may also experience changes in behavior during their personal lives, such as anger, agitation and sometimes even delusions or hallucinations.

There is not a cure and/or successful treatment for Alzheimer's. All the reported treatment methods do not show a light at the end of the tunnel. The results of the reported treatments are mostly either based on exercise, body treatment, or based on some herbal remedies and dietary supplements. One promising treatment reported by scientists at the University of South Florida promoting the most potent antioxidant EGCG (epigallocatechin-3-gallate), which is found in green tea. Scientists discovered if they treated the Alzheimer's patients with concentrated EGCG, it will reduce noticeable amount of their Beta-amyloid deposited in brain.

During the past few years, several breakthroughs for AD have been reported where all these breakthroughs are only effective on the early stages of Alzheimer's. Researchers from Rush University Medical Center in Chicago are working in gene transfer using very thin needles; inject the drug into the area of brain that deteriorates very early on Alzheimer's. This techniques and other similar methods are only promising if Alzheimer's has been detected at its early development.

If the patient is treated at the early stage of disease, the patient can have a relatively good life style even though he/she is not totally cured. Therefore, the diagnosis and early detection of Alzheimer's is highly desirable and it is in the world's interest. Many methods and suggestions are reported during the past decade in literatures and patent disclosures for Alzheimer's detection and diagnosis. Presently, there are no simple methods like blood or urine test that can detect Alzheimer's.

In the following there are several prior art methods presently used for early detection of Alzheimer's:

1. Testing the patient's memory by asking questions and studying the patient's family history to determine if Alzheimer's is present. This is not very reliable technique and it mostly is done by a family doctor as initial warning for Alzheimer's.
2. Brain scanning by such techniques as CT (computed tomography) and MRI (magnetic resonance imaging) could be used for AD diagnosis. The problem of these techniques is that they are only effective at the late stages of Alzheimer's which the damage is already done.
3. Researchers at New York University Medical Center have reported EEG (electroencephalogram) testing that measures electrical activity in the brain to pinpoint the early signs of Alzheimer's as warning signal. In this method, the measured brain activity of patient is compared to a standard activity of a patient with no Alzheimer's disease. This method still is at initial study stage and according to the scientists at Alzheimer's Association, there is concern that EGG study is too limited and the findings are too preliminary.
4. Researchers in the Netherlands reported that they can predict the early detection of Alzheimer's by measuring the size of two parts of the brain, the hippocampus, and amygdala. For those patients who have smaller sizes of these two parts against some standard have several time more likely to suffer from the Alzheimer's decease. The technique is still at study stage and mostly is looking for any type of dementia; they are not focusing on Alzheimer's. Another drawback of this technique is direct scanning of the brain which is likely harmful to patient.
5. There is a new technique recently reported by several institutes including Harvard Medical School and Brigham and Women's Hospital in Boston. The technique is detecting early phases of Alzheimer's disease by measuring the level of Beta-amyloid protein plaques deposited in the lens of the patient's eye using a non-invasive laser scanning and imaging. This new discovery could revolutionize early detections of Alzheimer's disease including most of the dementia disorders. All the previous measuring techniques have to use part of the brain for detection which is not advisable. The fact that the plaque (abnormal beta-amyloid protein) which deposits in the brain of Alzheimer's patient also will deposit simultaneously in the lens of the patient's eye similar to formation of cataracts, opens a new avenue for early diagnosis and continuous monitoring of Alzheimer's.

Among the above listed prior arts for early detection of Alzheimer's, the most promising technique is the last method, Alzheimer's diagnosis by laser scanning the lens of patient's eye. Laser imaging of the eye for AD detection has now been accepted among the researchers to be a promising technique.

One example is Sianto et al in U.S. Pat. No. 6,162,186 who is claiming that AD Patients' autonomic nervous system is hypersensitive to the neural transmitter mediators (NTM), used as eye drops, with concentration so low that did not affect the pupil's diameter change and other pupil's characteristics if applied on a person with no sign of being AD symptom. They use standard CCD camera to measure the change in a diameter and constriction of the pupil in the eye of an AD patient in a short time. For measuring the pupil's constriction velocity, the test is done under a low light with controlled intensity and duration. The inventors compare this data of an AD patient with some predefined standard data taken from normal persons.

Another example is Zhou et al, in U.S. Pat. No. 6,988,995 who is using a diode laser with 780 nm radiation. The laser light is first collimated and then scans in 2 dimensions by a resonance scanner and a galvanometer scanner. The scanned beam is taking data from the eye RNFL (retinal nerve fiber layers) compared with some standard signatures. The inventors claim that their method is using birefringence data of the structural elements of the eye with sufficient accuracy which is required to identify the effects of AD in the RNFL. The drawback of the invention is that there is no experimental data to support the invention. In this patent the laser power is not known and its safety is questionable. Even the inventors are not sure that the method is practical and there is no proof that the RNFL is affected by AD.

The present arts have at least three major drawbacks. The first one is high intensity laser scanning which is harmful to the patient's eyes and sometimes extremely dangerous if it has to penetrate inside the layers of the deposited plague. The second problem of the existing disclosed methods is the requirement of large, heavy, and expensive apparatus which makes testing inconvenient to be done in Doctors' office and the patient has to go to hospital. The third drawback is the lack of a very sensitive and highly efficient testing process which is required for early detection of the AD symptoms.

From the above discussions of the prior arts, the only presently known means of positively proving and demonstration of AD case in a person can only be achieved by a brain biopsy or a postmortem examination to determine existing of the plaque (amyloid) in brain tissue. It is overwhelmingly obvious that there has been remained at large demand for an accurate diagnosis for these AD symptoms which do not include brain biopsy, surgery, or even using the harmful high dose MRI and CT.

BRIEF SUMMARY OF THE DISCLOSED METHOD AND APPARATUS

The primary objective of the present method and apparatus is to provide new systems and technique for the early diagnosis of Alzheimer's Disease which is not involved brain surgery or biopsy. Based on the above background of the prior arts, it is clear that a precise and accurate measurement of the Alzheimer's deposited layers of amyloid (plaque) in the eyes of the patient is a possible solution.

The disclosed method and apparatus use terahertz waves instead of laser for scanning the eye of the AD patient to precisely image the amyloid layer non-invasively in real time to determine the deposited plaque of amyloid with very high resolution by dividing the amyloid layer thickness to a large number of very thin microlayers. Each microlayer independently is scanned by terahertz waves and all microlayers' images are integrated to generate a well defined signature of the AD patient eyes. The accuracy and high resolution of this method can easily distinguish the abnormality of an AD patient with the signature of a normal person and the signature of a person with common age-related cataracts.

Sensing with terahertz segment of spectrum has several significant advantages over sensing at other sides of spectrum. Terahertz radiation is completely unionized with photon energies more than six orders of magnitude less than soft x-rays. Most terahertz applications require less than one microwatt of power makes terahertz radiation completely safe for use by humans or on human subjects.

Terahertz waves are bounded between millimeters waves (less than $1\times10^{11}$ Hz) and photonics waves (greater than $1\times10^{13}$ Hz). The electromagnetic frequencies lower than terahertz band are covering mm waves (microwaves), while the electromagnetic frequencies higher than terahertz band are covering near infrared through visible spectrum.

Terahertz wave band can be used for time domain and frequency domain imaging. The present applications of terahertz waves are spectroscopy in atmospheric science and in astronomy, imaging for burn diagnostics, tomography, biomedical, medical diagnostics, screening for weapon, explosives, biohazard, imaging of concealed objects, cancerous tissue detection.

Existing water in living tissue limits the penetration depth of terahertz energy to a few millimeters, which is just sufficient for the diagnosis of RNFL which has a thickness of less than 200 microns. Terahertz waves above 0.5 THz can travel in air up to a meter, which is more than sufficient to transmit and receive signals from an eye test.

Besides detecting the presence of AD, the present method and apparatus is also valuable to determine how advance is the concentration of Amyloid plaques as well as information regarding whether the progression has stopped or has slowed down. A map showing, the difference between AD plaques and age-related cataracts, can aid in the accurate diagnosis of AD with no ambiguity. This is in contrast to the poor resolution of the prior art using laser techniques. When using terahertz systems such as disclosed herein, the combination of the spatial resolution and the high spectral resolution of a terahertz imaging system can be utilized to detect Alzheimer's progression with high level of confidence.

The present method and apparatus gathers data in three spatial dimensions. Initially, a spot is selected on the outer ring of the lens of the eye which is the location of the AD plaques deposition. The spot travels in depth where a line image is constructed resulting optical arrangement and synchronizing, using methods of optical coherence topography (OCT) and other similar methods. The depth of the RNFL is binned according to the desired spatial resolution, signal-to-noise ratio, and the characteristic of the rapid optical delay line. Then, the incident beam will be scanned in two directions collecting three dimensional data of a rectangular area alongside of the deposited ring. To improve the reliability of this method several rectangular areas of the outer ring of the patient's eye are selected for similar experiment. A tomography will then be constructed from the gathered overall data.

A better understanding could be achieved with reference to Detailed Description of the disclosed method and apparatus and with reference to the drawings. The description represents a particular case to realize the disclosed method and apparatus and is not intended to define the invention, but merely to provide adequate support for the claims appended hereto. Accordingly, the invention is defined solely by the claims to the invention appended hereto.

DETAILED DESCRIPTION

Figure 1:
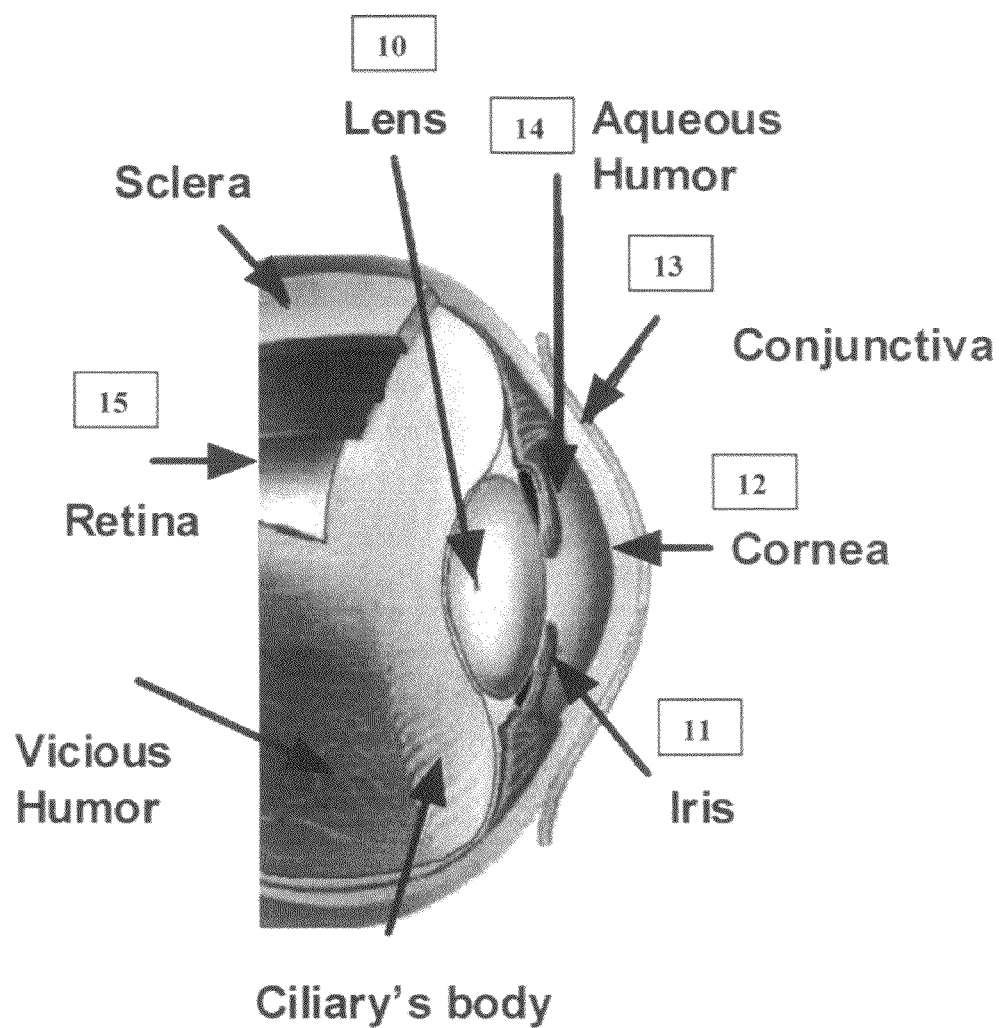
FIG. 1 is a diagram of the human eye showing its main structures.

FIG. 1 is a diagram of the human eye's structure which shows the lens 10 dimension relative to other elements of the eye. The lens focuses light rays onto the retina. An iris 11, the color part of the eye changes the amount of the light requires for optical processing. The eye acts as a perfect high resolution camera. It uses its variable index of reflection to dynamically focus a subject. Cornea 12 is bounded between conjunctiva 13 and aqueous Humor 14. Retina 15 works as an image processor to convert incoming rays into nerves signals where the brain analyzes the signals and creates the image.

Figure 2:
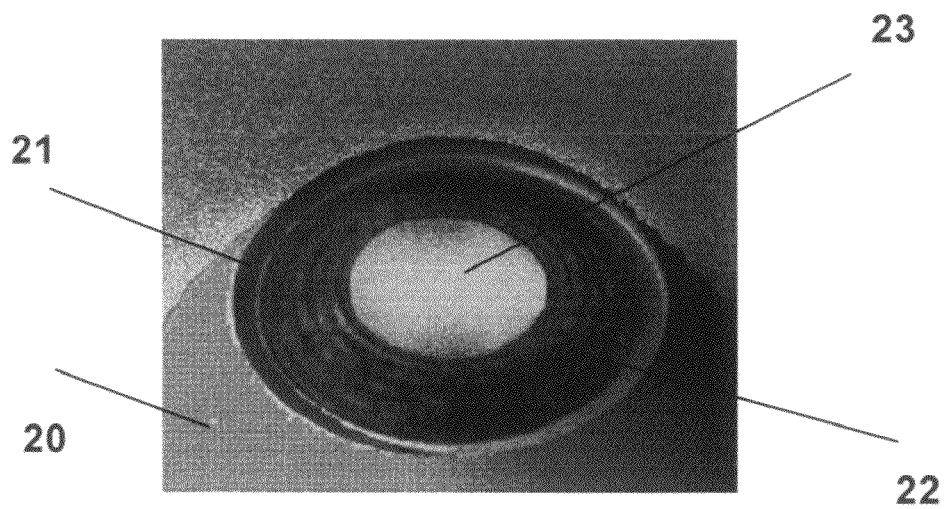
FIG. 2 is characterization and data in the lens of Human's eye
Figure 3:
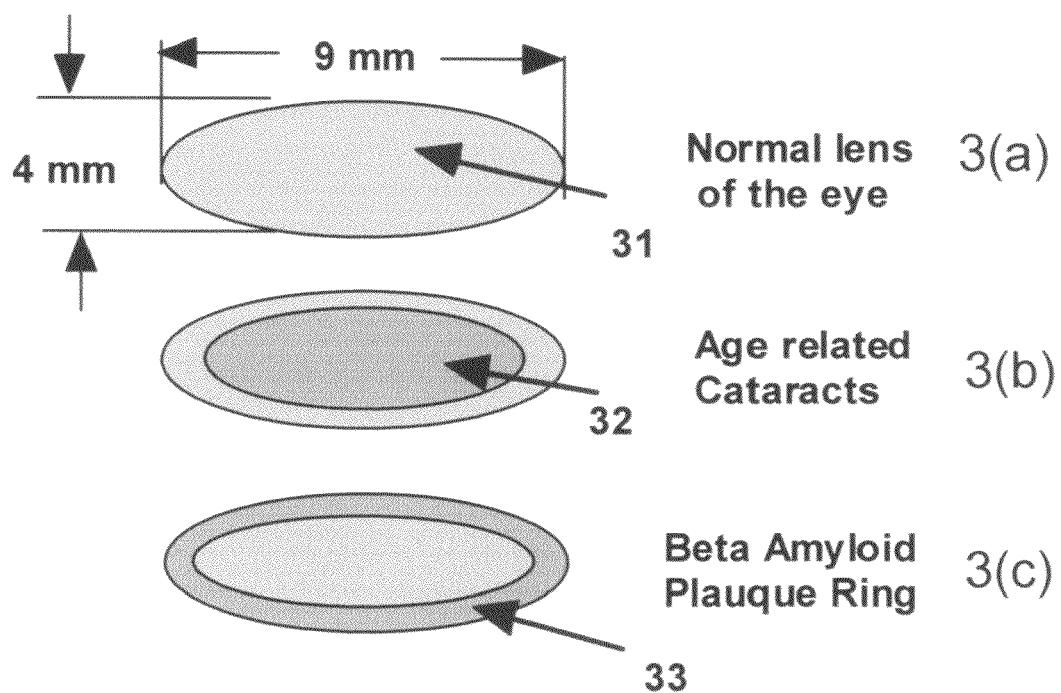
FIG. 3 is Alzheimer's signature compared with age related cataracts

FIG. 2 is a close up picture of the eye 20 where the lens 21 is partially exposed by iris 22 acts as a diaphragm and partially exposed the lens in the opening pupil 23. The lens normal characteristics have shown in FIG. 2. FIG. 3 shows a comparison between Alzheimer's plaques deposited in the lens of the patient's eye and the cataracts plaques deposited similarly in the lens of the eye in age related cataracts symptom. The lens of the eye 31 has a dimension of 9 mm in length and 4 mm in thickness. The thickness of the plaques deposited is normally about 200 microns and most likely the plaque is deposited in different locations. FIG. 3(a) shows the lens coloration 31 of an ordinary person. The age related cataracts patient, see FIG. 3 (b), where the plaques 32 is deposited in the center of the lens while the Alzheimer's patient with the Beta amyloid plaques 33 have the same dark coloration, see FIG. 3(c), but is deposited as a ring in the outward portion of the lens.

Figure 4:
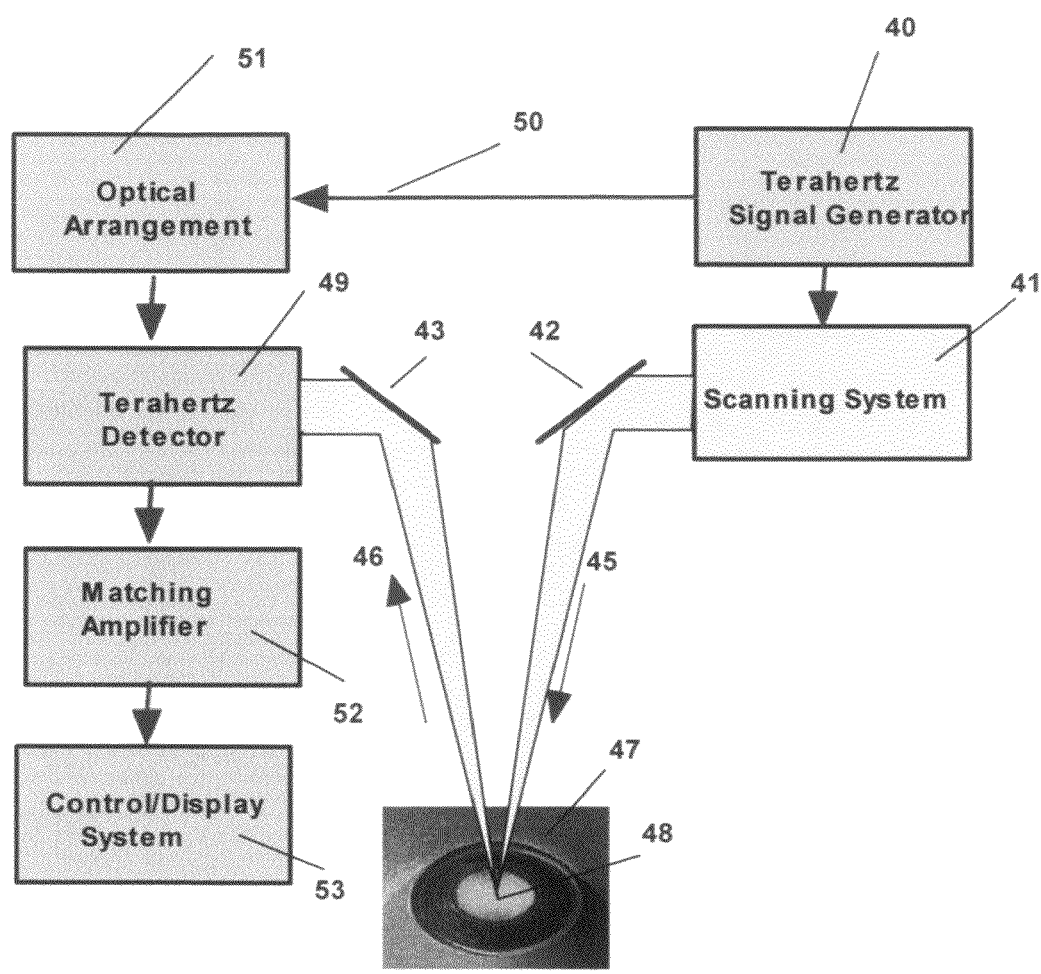
FIG. 4 is a simplified diagram of the THz scanning the lens of Patient's eye using both standard methods of time domain and frequency domain tomography.

The FIG. 4 is a simplified diagram of the THz scanning the lens of Patient's eye using standard methods of both time domain (TD) and frequency domain (FD) tomography. A tailored source of terahertz signal generator 40 is fed to the scanning system 41. Scanning system 41 includes positioner and, collimation and focusing optics where the focused THz rays are directed by mirror 42 on the lens of the patient's eye and positioned at specific location 48. The THz rays are focused at one point, stays at that point until travel inside the eye lens creating data of depth layers, and then it scans to the next point until the required area is 3-D scanned. Based on the doctor's requirement positioner can select different location for collecting similar data. The reflections of THz rays from the patient's eye are redirected to Terahertz detector 49 via mirror 43. The terahertz signal generator 40 generates both pulsed Terahertz and Terahertz frequency sweeps sources for TD and FD methods respectively. These sources are transmitted to optical arrangement system 51 through line 50. Optical Arrangement system 51 creates variable optical delay lines and local sweep oscillators to feed to detector 49 for TD and FD methods respectively. The Terahertz detector 49 extracts eye lens data using variable delay lines in the case of the TD method and local sweep oscillators and mixer in the case of FD method and transfer data to matching amplifier system 52 and then the collected data will arrive in control/display system 53 where the overall eye data is analyzed and the results is sent electronically to the patient's medical report.

The scanning system is dynamically synchronized to the scanned terahertz signals that are illuminating the eye lens.

Terahertz signal generator covers terahertz bandwidth from 200-10000 GHz.

The detector can detect a difference signal from the reflected terahertz signal from the eye lens and a reference signal from the terahertz signal generator or a difference signal from the reflected terahertz signal from the eye lens and a local sweep generator signal.

The system further uses a matching amplifier to improve the detected signal. The system can further provide a three dimensional image of the eye lens in real time which includes compositional information about the eye lens.

An image is formed from the reflected pulses at each layer perpendicular to the eye lens surface and is comprised of a plurality of horizontal bands, each band being adjacent to another, with equal bandwidths. The images will be compared with a calibrated reference stored in memory, indicating regions of coincidence and region of non-coincidence, and the images are combined at different layers to obtain the tomography of the deposited Amyloid layers of the eye lens.

The result will be a three dimensional image of the eye lens in real time which includes compositional information about the eye lens.

We claim:

1. A method for early diagnosis of Alzheimer, comprising:
   a) generate a Terahertz signal;
   b) split the Terahertz signal to a scanning system and an optical arrangement;
   c) feed a signal passing though the optical arrangement to a Terahertz detector;
   d) illuminate the eye lens with a focused scanning Terahertz beam from the scanning system;
   e) redirecting the reflection of the eye lens into the Terahertz detector;
   f) inserting the output of the Terahertz detector to an amplifier;
   g) inserting the output of the amplifier to a control and display system;
   h) wherein the method measures the amyloid layer of the eye and provides an early diagnosis of Alzheimer's disease.

2. The method of claim 1, further comprising using a scanning system dynamically synchronized to the scanned terahertz signal that are illuminating the eye lens.

3. The method of claim 1, wherein the Terahertz signal generator covers terahertz bandwidth from 200-10000 GHz.

4. The method of claim 2, further comprising setting up a terahertz detector to detect either a difference signal from the reflected terahertz signal from the eye lens and a reference signal from the Terahertz signal generator, or a difference signal from the reflected terahertz signal from the eye lens and a local sweep generator signal.

5. The method of claim 1, further comprising using a second amplifier to improve the detected signals.

6. The method of claim 1, further comprising forming an image from the reflected pulses at each layer perpendicular to the eye lens surface.

7. The method of claim 1, further comprising:
   a. comparing the images with a calibrated reference stored in memory;
   b. combining the images at different layers to obtain the tomography of the Amyloid layer in eye lens;
   c. indicating regions of coincidence and region of non-coincidence; and
   d. showing the result in control and display system.

8. The method of claim 6, further providing a three dimensional image of the eye lens in real time which includes compositional information about the eye lens.

9. The method of claim 7 wherein the image is comprised of a plurality of horizontal bands, each band being adjacent to another, with equal bandwidths.

* * * * *